(12) United States Patent
Hall et al.

(10) Patent No.: US 10,261,071 B2
(45) Date of Patent: Apr. 16, 2019

(54) VOLATILE ORGANIC COMPOUNDS AS DIAGNOSTIC BREATH MARKERS FOR PULMONARY OXYGEN TOXICITY

(71) Applicants: Richard T. Mahon, Germantown, MD (US); Aaron A Hall, Clarksburg, MD (US); William A Cronin, Bethesda, MD (US)

(72) Inventors: Aaron A. Hall, Clarksburg, MD (US); Richard T. Mahon, Germantown, MD (US); William A. Cronin, Bethesda, MD (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 99 days.

(21) Appl. No.: 15/644,793

(22) Filed: Jul. 9, 2017

(65) Prior Publication Data
US 2018/0180590 A1    Jun. 28, 2018

Related U.S. Application Data

(60) Provisional application No. 62/361,801, filed on Jul. 13, 2016.

(51) Int. Cl.
| | | |
|---|---|---|
| *G01N 33/497* | (2006.01) | |
| *G06F 19/00* | (2018.01) | |
| *G01N 30/72* | (2006.01) | |
| *G01N 30/88* | (2006.01) | |

(52) U.S. Cl.
CPC ....... *G01N 33/497* (2013.01); *G01N 30/7206* (2013.01); *G06F 19/707* (2013.01); *G01N 30/72* (2013.01); *G01N 2030/884* (2013.01); *G01N 2033/4975* (2013.01); *G01N 2560/00* (2013.01); *G01N 2800/12* (2013.01); *G01N 2800/50* (2013.01)

(58) Field of Classification Search
USPC ...................................................... 250/282
See application file for complete search history.

(56) References Cited

U.S. PATENT DOCUMENTS

| | | | | |
|---|---|---|---|---|
| 2010/0305084 A1* | 12/2010 | Castanedo | ............ | C07D 487/04 514/186 |
| 2012/0202785 A1* | 8/2012 | Heald | .................. | C07D 401/12 514/210.18 |
| 2016/0058758 A1* | 3/2016 | Blonngren | ......... | A61K 31/4985 514/233.2 |

OTHER PUBLICATIONS

Clark, J.M. and C.J. Lambertsen, Pulmonary oxygen toxicity: a review. Pharmacol Rev, 1971. 23(2): p. 37-133.
Jenkinson, S.G., Oxygen toxicity. New Horiz, 1993. 1(4): p. 504-11.
(Continued)

*Primary Examiner* — Kiet T Nguyen
(74) *Attorney, Agent, or Firm* — Albert M. Churilla; Ning Yang (57) ABSTRACT

A set of volatile organic compounds is provided, comprising Benzene, 2,3,4-trimethyl-Pentane, 1,4-dimethyl-, trans-Cyclohexane, 2,2,4-trimethyl-Hexane, 1,7,7-trimethyl-Tricyclo[2.2.1.0(2,6)]heptane, and 4-ethyl-3-Octene for breath analysis. Methods of identifying these VOCs and use thereof in diagnosing, monitoring the onset of pulmonary toxicity are also disclosed.

15 Claims, 6 Drawing Sheets

(56) References Cited

OTHER PUBLICATIONS

Mikkelsen, M.E., et al., Can we optimize long-term outcomes in acute respiratory distress syndrome by targeting normoxemia? Ann Am Thorac Soc, 2014. 11(4): p. 613-8.
Jackson, R.M., Pulmonary oxygen toxicity. Chest, 1985. 88(6): p. 900-5.
Crapo, J.D., Morphologic changes in pulmonary oxygen toxicity. Annu Rev Physiol, 1986. 48: p. 721-31.
Hedley-Whyte, J., Pulmonary oxygen toxicity: investigation and mentoring. Ulster Med J, 2008. 77(1): p. 39-42.
Deneke, S.M. and B.L. Fanburg, Normobaric oxygen toxicity of the lung. N Engl J Med, 1980. 303(2): p. 76-86.
Freeman, B.A. and J.D. Crapo, Hyperoxia increases oxygen radical production in rat lungs and lung mitochondria. J Biol Chem, 1981. 256(21): p. 10986-92.
Dent, A.G., T.G. Sutedja, and P.V. Zimmerman, Exhaled breath analysis for lung cancer. J Thorac Dis, 2013. 5 Suppl 5: p. S540-50.
Phillips, M., et al., Point-of-care breath test for biomarkers of active pulmonary tuberculosis. Tuberculosis (Edinb), 2012. 92(4): p. 314-20.
Phillips, M., et al., Effect of oxygen on breath markers of oxidative stress. Eur Respir J, 2003. 21(1): p. 48-51.
Van Ooij, P.J., et al., Nitric oxide and carbon monoxide diffusing capacity after a 1-h oxygen dive to 9 m of sea water. Clin Physiol Funct Imaging, 2014. 34(3): p. 199-208.
Council, N.R., Guide for the Care and Use of Laboratory Animals. 1996, Washington, DC: The National Academies Press. 140.
Phillips, M., et al., Detection of an extended human volatome with comprehensive two-dimensional gas chromatography time-of-flight mass spectrometry. PLoS One, 2013. 8(9): p. e75274.
Wang, B., et al., DISCO: distance and spectrum correlation optimization alignment for two-dimensional gas chromatography time-of-flight mass spectrometry-based metabolomics. Anal Chem, 2010. 82(12): p. 5069-81.
Phillips, M., et al., Rapid point-of-care breath test for biomarkers of breast cancer and abnormal mammograms. PLoS One, 2014. 9(3): p. e90226.
Clark, J.M., Pulmonary limits of oxygen tolerance in man. Exp Lung Res, 1988. 14 Suppl: p. 897-910.
Van De Water, J.M., et al., Response of the lung to six to 12 hours of 100 per cent oxygen inhalation in normal man. N Engl J Med, 1970. 283(12): p. 621-6.
Bos, L.D., M.J. Schultz, and P.J. Sterk, Exhaled breath profiling for diagnosing acute respiratory distress syndrome. BMC Pulm Med, 2014. 14: p. 72.
Poli, D., et al., Exhaled volatile organic compounds in patients with non-small cell lung cancer: cross sectional and nested short-term follow-up study. Respir Res, 2005. 6: p. 71.
Sethi, S., R. Nanda, and T. Chakraborty, Clinical application of volatile organic compound analysis for detecting infectious diseases. Clin Microbiol Rev, 2013. 26(3): p. 462-75.
Loiseaux-Meunier, M.N., et al., Oxygen toxicity: simultaneous measure of pentane and malondialdehyde in humans exposed to hyperoxia. Biomed Pharmacother, 2001. 55(3): p. 163-9.
Morita, S., M.T. Snider, and Y. Inada, Increased N-pentane excretion in humans: a consequence of pulmonary oxygen exposure. Anesthesiology, 1986. 64(6): p. 730-3.
Bernard, G.R., et al., The American-European Consensus Conference on ARDS. Definitions, mechanisms, relevant outcomes, and clinical trial coordination. Am J Respir Crit Care Med, 1994. 149(3 Pt 1): p. 818-24.
Buszewski et al, Human exhaled air analytics: biomarkers of diseases. Biomed. Chromatogr. 21: 553-566 (2007).
Gelfand, et al., Dynamic respiratory response to abrupt change of inspired CO2 at normal and high PO2. Journal of applied physiology vol. 35, No. 6, Dec. 1973.

* cited by examiner

For sample $i$, the abundance for peak $j$, $A_{ij}$ is used to calculate a subscore by $$Q_{ij} = \begin{cases} w_j \; if \; \begin{cases} S_j = 1 \; \& \; A_{ij} > C_j \\ S_j = -1 \; \& \; A_{ij} < C_j \end{cases} \\ 0, otherwise \end{cases}$$

VOLATILE ORGANIC COMPOUNDS AS DIAGNOSTIC BREATH MARKERS FOR PULMONARY OXYGEN TOXICITY

CROSS REFERENCE TO RELATED APPLICATIONS

The present application claims the benefit of Provisional Application Ser. No. 62/361,801, filed on Jul. 13, 2016, the entire contents of which are hereby incorporated by reference.

GOVERNMENT SUPPORT

This invention was supported in part with funding provided by the Defense Medical Research Development Program, work unit #60311HP.3730.001.A1270. The government has certain rights to this invention.

FIELD OF THE INVENTION

The present invention relates to a novel set of volatile organic compounds (VOCs) that are indicative of onset of pulmonary oxygen toxicity ($POT_2$), the methods of detecting and reducing/preventing pulmonary injuries caused by prolonged high concentration oxygen exposure, or $POT_2$ using the novel set of VOCs and the method for identifying volatile organic compounds predictive of onset of pulmonary oxygen toxicity.

BACKGROUND

Oxygen has diverse applications in military operations and in clinical settings. While oxygen comprises 21% of the air that we breathe, human bodies are not adapted to higher levels of oxygen, and exposure to increased oxygen for an extended duration can be harmful. To minimize oxygen toxicity in clinical settings, the fractional inspired oxygen (FiO2) is typically titrated to maintain a hemoglobin saturation of >90% [4, 5]. However, there are clinical scenarios such as acute lung injury (ALI), acute respiratory distress syndrome (ARDS) and refractory hypoxemia, in which a FiO2>60% may be required to prevent end-organ damage [3]. Additionally, it is not uncommon for pilots, divers, and astronauts to inhale high concentrations of oxygen prior to operations in order to reduce the risk of decompression sickness. In these scenarios, lung injury known as pulmonary oxygen toxicity ($PO_2T$) may develop.

$PO_2T$ is a progressive disease defined clinically by acute tracheobronchitis, which manifests as cough and burning sensation with respiration, absorption atelectasis, pulmonary edema, acute parenchymal lung injury, and/or chronic lung injury [2]. Clinical signs include detrimental changes in vital capacity [6], lung compliance and diffusing capacity, radiographic evidence of non-cardiogenic edema, rales on auscultation, or a decreased ratio of arterial oxygen partial pressure ($PaO_2$) to the $FiO_2$. Histologically, $PO_2T$ is divided into two phases: the acute exudative phase (characterized by edema, hemorrhage, swelling and cellular destruction) and the chronic proliferative phase (transition to interstitial fibrosis and proliferation of type II alveolar epithelial cells) [7]. Unfortunately, by the time current diagnostic modalities detect injury, significant pulmonary damage has already occurred. Without a direct measure to identify $PO_2T$, it is impossible to predict the point at which increasing lung injury is being sustained during oxygen administration.

Detecting $PO_2T$ early, and ameliorate or prevent $PO_2T$ will likely decrease mortality and shorten the length of hospitals stay that requiring the use of supplemental oxygen. In addition, detecting $PO_2T$ in operational settings will better guide operation decisions, and return to duty decisions allowing for improved military readiness. The lack of biomarkers to directly measure the early onset of $PO_2T$ represents significant gaps in this capability, and hinders the detection, diagnosis, and prevention/reduction of $PO_2T$.

Breath analysis of specific volatile organic compounds (VOCs) has long been recognized as a reliable technique for diagnosing certain medical conditions including tissue inflammation (e.g. asthma), immune responses (e.g. to cancer cells or bacteria), metabolic disorders (e.g. diabetes), digestive processes, liver and/or kidney disorders, gum disease, halitosis, and other physiological conditions [27]. To date, more than 3,000 VOCs have been detected in exhaled breath. Of these compounds, about 1% are likely to contain disease-specific VOCs, such as alkanes, isoprenes, benzenes and methyl alkanes. Gas chromatography-mass spectrometry (GC-MS) and absorption spectrometry have been employed to measure VOCs in exhaled breath samples, and to create a VOC profile.

Recent human and animal research has demonstrated that prior to the onset of clinical symptoms, hypoxia induced significant oxidative stress that overwhelms inherent antioxidant enzymes and leads to lipid peroxidation [8, 9]. To date, breath biomarker research in the setting of oxygen exposure is limited to two studies. Biomarkers were detected in as little as 30 minutes of hyperoxic exposure in otherwise asymptomatic individuals [12]. Similarly, significant changes in exhaled molecular profiles of five VOCs were observed after submerged oxygen diving (Va Pojj et al. Respiratory physiology. 2014). However, no correlation has been reported between the presence of these VOCs, and relevant clinical endpoints of onset of $PO_2T$, which is the objective of this invention. This application discloses a novel set of volatile organic compounds (VOCs) that can be used as noninvasive biomarkers for the detection of onset of $PO_2T$ in reduction and prevention of pulmonary injury or $PO_2T$ and to guide safe clinical oxygen use.

DETAILED DESCRIPTION OF THE FIGURES

FIG. 2 shows changes in abundance from baseline to exposure for both oxygen exposed and room air exposed subjects graphed with log (abundance of breath—abundance of air) on the x-axis and density on the y-axis.

FIG. 3 is a representative schematic of the VOC content collected from breath exhalate samples over the course of the exposure. The x-axis represents the ROC/AUC score (probability) that a VOC collected from an oxygen-exposed swine will change from baseline during the exposure period. The y-axis represents the ROC/AUC score that a VOC collected from the oxygen-exposed swine during the exposure period will be present in the breath samples collected from air-exposed swine during the exposure period. The symbol shape represents the prevalence (proportion of the samples the VOC is present in), the symbol size represents the relative abundance of the VOC in a given breath sample, while the shading represents the p-value for the difference in the ROC/AUC value from 0.5 (random chance) to 1.0 (perfect sensitivity and specificity). Cut-off values used for biomarker screening were 0.625 for the x-axis and 0.6 for the y-axis yielding 18 candidate VOCs.

DETAILED DESCRIPTION OF THE INVENTION

As used herein, the term "pulmonary injury" is defined by the $PaO_2/FiO_2$ ratio<350 millimeters of mercury [mmHg].

As used herein, the term "exudative phase of $PO_2T$" is defined as presentation of pathologic changes, including interstitial edema, congestion and thickening of alveolar septa by inflammatory cells with and without type II pneumocyte hyperplasia.

As used herein, the term "Pulmonary Oxygen Toxicity" or $PO_2T$ is defined as pulmonary injuries caused resulting from the harmful effects of breathing molecular oxygen at increased partial pressures, such as prolonged high concentration oxygen exposure.

As used herein, the term "onset of $POT_2$" is defined generally as the exudative phase of $PO_2T$.

The invention also discloses a novel set of VOCs, and the methods of detecting, and preventing/reducing $PO_2T$ using said novel set VOCs in a breath sample.

According to a first aspect, the present invention provides a method for identifying a set of VOCs that are indicative of onset of pulmonary oxygen toxicity comprising the steps of: a) collecting breath samples from subjects before and after exposure to oxygen enriched atmosphere ($FiO_2>60\%$); b) determining the levels of volatile organic compounds in said breath samples; c) comparing the levels of volatile organic compounds in breath samples taken after said oxygen exposure to levels of volatile organic compounds in breath sample from the same subject taken before said oxygen exposure; d) identifying a set of volatile organic compounds that shows significantly change in breath samples collected before and after said oxygen exposure; and e) producing a diagnostic algorithm based on the change profile of said set of volatile organic compounds that is indicative of onset of pulmonary oxygen toxicity.

The change pattern of each volatile organic compound in a breath sample may be analyzed with a pattern recognition analyzer. The said pattern recognition analyzer include but is not limited to algorithm analysis method group consisting of principal component analysis (PCA), artificial neural network algorithms, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

The level of each volatile organic compound may be measured using a variety of techniques, such as Gas-Chromatography (GC), GC-lined Mass-Spectrometry (GC-MS), Proton Transfer Reaction Mass-Spectrometry (PTR-MS), Electronic nose device, or Quartz Crystal Microbalance (QCM).

According to another aspect, this invention provides a method to detect the onset of pulmonary oxygen toxicity in a subject comprises the following steps: collecting a breath sample from a subject who has been exposed to an oxygen enriched atmosphere; detecting in said breath sample the level of six volatile organic compounds including benzene; 2,3,4-trimethyl pentane; 1,4-dimethyl-trans cyclohexane; 2,2,4-trimethyl-hexane; 1,7,7-trimethyl-tricyclo heptane; and 4-ethyl-3-octene; and predicting an onset of pulmonary oxygen toxicity in said subject. In one embodiment, the presence of all six volatile organic compounds in a breath sample indicates the onset of pulmonary oxygen toxicity in the subject. In another embodiment, when significant difference in levels of these volatile organic compounds in the breath samples taken before and after exposing the subject to an oxygen enriched atmosphere is indicative of onset of pulmonary oxygen toxicity. For example, divers, piolet and astronauts may provide a breath sample before and after exposures to oxygen enriched atmosphere (i.e. inhaled air with high $FiO_2$). When levels of this novel set of volatile organic compounds are found to be significantly different in a subject's breath sample taken after such oxygen exposure when compared to his/her breath sample collected before the exposure, the change in level of the set of volatile organic compounds is indicative of the onset of pulmonary toxicity in the subject. The subject (diver, point and astronauts)'s condition can be monitored for pulmonary injuries and further injury can be prevented or reduced by limit future exposure to high concentration oxygen. For example, the frequency or duration of exposure to high concentration oxygen can be restricted, and the concentration of the oxygen exposed to can be reduced, thus preventing or reducing $PO_2T$.

In yet another embodiment. A breath score greater than −3.5 is indicative of risk of developing PO$_2$T. A breath score of 0.707-0.72 is indicative of the onset of injuries caused by pulmonary oxygen toxicity.

The breath score is calculated as follows:

$$Q_{ij} = \begin{cases} w_j \text{ if } \begin{cases} S_j = 1 \ \& \ A_{ij} > C_j \\ S_j = -1 \ \& \ A_{ij} < C_j \end{cases}, \\ 0, \text{ otherwise} \end{cases}$$

where the weights $w_j$, the signs $S_j$ and the cutoff values $C_j$ are taken from the sign and cutoff columns in the table 1. So each peak (j) will have a value of w, or 0 depending on the sign ($S_j$) and the relationship between $A_j$ and $C_j$. Then, the diagnostic score $Q_i$ for each sample i (representing 1 breath test) is $Q_i = \Sigma_j Q_{ij}$, which represents the sum of the w values or 0 values for each peak (j) used for the breath test.

The level of the volatile organic compound may be measured via a variety of techniques such as Gas-Chromatography (GC), GC-lined Mass-Spectrometry (GC-MS), Proton Transfer Reaction Mass-Spectrometry (PTR-MS), Electronic nose device, or Quartz Crystal Microbalance (QCM).

In yet another aspect, this invention provide a method of preventing or reducing pulmonary oxygen toxicity, which comprises the steps of a) collecting a breath sample from a subject at risk of developing pulmonary oxygen toxicity; b) measuring the level of organic volatile compounds selected from the group consisting of benzene; 2,3,4-trimethyl pentane; 1,4-dimethyl-trans cyclohexane; 2,2,4-trimethylhexane; 1,7,7-trimethyl-tricyclo heptane; and 4-ethyl-3-octene; c) predicting onset of pulmonary oxygen toxicity; and d) reducing said subject's exposure to oxygen enriched atmosphere if onset of pulmonary oxygen toxicity is predicted in step c). The exposure can be restricted and reduced by limit the frequency or duration of future exposure to high concentration oxygen, and by lowering the concentration of the oxygen the subject is exposed to. Thus preventing or reducing PO$_2$T. Alternatively, the subject who is showing onset of pulmonary oxygen toxicity can be treated with suitable medication.

Example 1: Identification of VOCs Using Swine Model

Materials and Methods

Animals

Male Yorkshire swine (n=22; 29.52±3.2 kilograms; Biotechnical Industries, Dunsborough, Pa.) were examined by a veterinarian upon delivery and housed in free-running cages at the animal care facility for five days before any procedures. Animals were provided a 12 hour light/dark cycle, water ad libitum, and twice daily feedings (2-2.5% body weight; Lab Diet Pig Grower, ASAP Animal Specialties and Provisions, Elkridge, Md.).

Surgical Preparation

Swine underwent vascular access port (VAP) placement and external carotid artery cannulation 72 hours prior to the experiment to allow recovery from surgical procedures before exposure. Anesthesia induction was performed with ketamine (20 milligrams per kilogram [mg/kg]; Ketathesia USP Injection 100 milligrams per milliliter [mg/mL]; Henry Schein Animal Health, Dublin, Ohio) and intramuscular xylazine (2 mg/kg; Anased Injection 100 mg/ml; Lloyd Shenandoah, Iowa). After induction, animals were endotracheally intubated and maintained on isoflurane inhalant anesthesia (1-3%; Halocarbon Products, River Edge, N.J.). Catheterization was performed using a 5-7 centimeter (cm) cranio-caudal incision in the ventral neck over the left or right carotid artery. Blunt and sharp dissection was used to expose and isolate the carotid artery, which was then cannulated with a 14-french intravascular catheter. Once inserted, the catheter was unclamped to confirm placement and flushed with heparinized saline. For placement of the port, a 5-6 cm curvilinear incision was made just dorsal and cranial to the right or left scapula. Subcutaneous tissues were undermined to create a pocket for the port and the catheter was tunneled between the skin and the subcutaneous tissues and attached to the VAP (Solomon Scientific, Skokie, Ill.). The port was then secured to the underlying musculature and functionality was confirmed by performing a 3 mL blood draw from the port. Subcutaneous tissues were closed with 2-0 suture and skin incisions were closed with a skin stapler.

Functionality of the VAP was again confirmed by performing a 3 mL blood draw. The port was then flushed with normal saline and locked with 1 mL heparin (1000 International Units [IU]/mL). An overlying occlusive bandage was placed over the carotid cut-down site and secured with Elastikon.

Study Design and Environmental Exposure

Following a four day recovery from VAP surgery, swine were randomized into two treatment groups:

Air Control Group: (20.9% FiO2 for 72 hours):(n=12)

Oxygen Group: (>95% FiO2 for 72 hours):(n=10)

Individual animals were placed in a custom-made Plexiglas run and exposed to room air for three background VOC samples spaced 12 hours apart. Immediately following the third VOC sampling, the box atmosphere was switched to the appropriate exposure (room air or oxygen). Oxygen exposure was considered initiated when the FiO2 reached>95% within the Plexiglas box (less than two minutes from gas switch). These conditions were maintained for 72 hours at normobaric pressure (1 atmosphere [ATM]). Air composition of the Plexiglas runs was monitored with a Gas Analyzer (Alpha Mega 9600, Lincoln, R.I.) and maintained at a stable temperature of 24 degrees Celsius (±0.22° C.), 76.9% (±0.96%) humidity, and <0.05% (±0.05%) carbon dioxide (CO2). Animals had free access to food and water throughout the treatment period.

The schedule of sample collection was as follows: for all animals, three baseline samples (breath exhalate, blood, and physiologic recordings) were collected every 12 hours for 36 hours with the animal breathing room air prior to randomization. Samples were then collected after 12, 24, 36, 48, 60, and 72 hours of treatment exposure.

Breath Exhalate Sample Collection

Breath exhalate samples were collected in awake, non-sedated swine via a solvent trap (Carbotrap, PerkinElmer, Waltham, Mass.) attached to a nose cone. Prior to sample collection animals were maintained on a breathing circuit via the nose cone supplied with room air or >95% FiO2 for a minimum of four minutes prior attaching the solvent trap. The solvent trap was then connected for four minutes to collect an exhaled breath volume equivalent to two liters of alveolar breath. A separate background sample of breathing circuit gas was also collected.

Each breath exhalate and paired background sample was stored at room temperature. After all study samples were collected, the samples were shipped overnight to Menssana Research, Inc. Breath Research Laboratory (Newark, N.J.) for analysis. Sample processing and analysis are detailed in the statistics section.

Arterial Blood Gas Analysis

Arterial blood gas samples were collected from the VAP using a 1 mL heparinized arterial blood sample syringe (Smiths Medical ASD, Inc., Keene, N.H.) connected to a 22 gauge POSI-GRIP™ Huber needle (Access technologies, Skokie, Ill.). The sample was then analyzed using an ABL800 flex bench-top blood gas analyzer (Radiometer America Inc., Brea, Calif.) for $PaO_2$ and PaCO2 content.

Physiological Monitoring

Respiration signals were detected using a Rheoencephalogram KR-Ea Rheo Preamp (OTE Galileo, Italy) connected to a PowerLab (ADInstruments) data acquisition device. The Rheoencephalogram consists of an analog channel connected to two electrode cables connected to gel electrodes positioned on either side of the ribcage. Electrocardiogram (ECG) signals were detected using a Bioamplifier (Gould) connected to a PowerLab data acquisition device. The Bioamplifier consists of an analog channel connected to four electrode cables. The electrode cables were connected to four gel electrodes positioned on the left shoulder, right shoulder, left subcostal area, and right subcostal area. Respiration and ECG data were recorded and analyzed in LabChart software on a laptop that connected to the PowerLab.

Histologic Assessment of Lung Injury

Partial necropsies were performed on all animals after 72 hours of treatment. The right lung was collected for measurement of wet-dry ratios. The left lung was fixed via tracheal instillation at a standard pressure of 25 cmH20 with 10% neutral buffered formalin. The lungs were then sectioned into ten, one centimeter (cm) cranial to caudal serial sections. Three, 1 cm blocks were cut from each section and post-fixed in 10% neutral buffered formalin, trimmed, embedded in paraffin and cut into 5 µm sections for histological staining. Histology slides were de-paraffinized and stained with hematoxylin and eosin. A board-certified veterinary pathologist blinded to group randomization reviewed all gross necropsies, images, and histology slides.

For quantitative histologic measurement of interstitial pulmonary edema, bright-field photomicrographs of the stained slides were captured using an Olympus AX80 microscope (Olympus Corporation, Tokyo, Japan) equipped with a ×1.25 Olympus plan Apo objective and an Olympus DP70 digital camera. Photomicrographs were saved in .tiff file format for analysis using ImageJ64 (Rasband, W. S., ImageJ, US National Institutes of Health, Bethesda, Md., USA; http://imagej.nih.gov/ij/, 1997-2011). ImageJ analysis was performed by a trained observer blinded to group randomizations. Each lung histology image was opened using the ImageJ program and converted to grayscale. The interstitium was outlined using the polygon tool and the background deleted using the clear outside function. The interstitial space was then quantified using the measure function and divided by the total area of the lung section. A ratio of total interstitial area to total section area was determined. The percentage interstitial area of three sections per lung sample was determined and averaged over 10 lung samples. The percentage area of interstitial edema was derived as the mean from all 30 samples per lung. The mean percentage area of interstitial edema for all of the lungs in each treatment group was compiled into a spreadsheet utilizing MICROSOFT EXCEL® (2011) for downstream statistical analysis.

Statistical Analysis

Physiological data and histology: All statistical calculations were performed using statistical software (Graphpad Prism, La Jolla, Calif. USA). A student's t-test was used for statistical analysis of continuous variables between two groups. A one-way repeated measures ANOVA was used to compare one factor in three or more groups. A two-way repeated measures ANOVA compared two factors in three or more groups. If an overall significance was found, a post hoc comparison was made using the Bonferroni Test. A two-tailed p-value<0.05 was considered statistically significant.

VOC analysis: The analysis methods are well described elsewhere [15]. Briefly, carbotrap tubes containing exhaled breath were thermally desorbed to elute trapped VOCs and then processed via two-dimensional gas chromatography-mass spectrometry (GC-MS). For each detectable peak, the retention time in each dimension, mass/charge ratio and abundance were calculated and recorded. The retention time data and mass/charge ratios provided tentative identification for each compound using the National Institute of Standards and Technology (NIST) compound library. Chromatogram data from the two-dimensional GC/MS analysis were aligned statistically as described previously [16]. Prospective biomarkers of oxygen exposure were identified by comparing baseline samples with post-exposure samples in the oxygen-exposed swine, and comparing the post-exposure samples between air and oxygen samples. This comparison yielded 18 samples with a receiver operating characteristic area under the curve (ROC AUC) score greater than a predetermined cutoff of 0.6. From these 18 samples, weighted digital analysis (WDA) was used to narrow down a subset of 6 VOCs, which were predictive of pulmonary injury (as defined by the $PaO_2/FiO_2$ ratio<350 millimeters of mercury [mmHg]) to construct a predictive algorithm or breath score for $PO_2T$.

Development of Algorithm for Determination of Breath Score Indicative of Pulmonary Oxygen Toxicity Aggregate Breath Score (ABS) and Physiologic Data:

In reviewing breath score with the physiologic data of the arterial blood gases, a ROC curve was created for breath score prediction of $PaO_2/FIO_2$ ratio<350 mmHg. The AUC of the updated ROC curve remained essentially unchanged at 0.78. Specific peak values $A_{ij}$ are calculated by integrating using the quant-mass m/z in the table, and then normalizing the peak area to the area of the internal standard. Peak s are included if their first retention time (RT1) is within 5 s and second retention time (RT2) is within 0.1 S of the time in the Table 1.

TABLE 1

| Possible Chemical Name | m/z | RT1 (s) | RT2 (s) | weight | Sign | cut-off |
|---|---|---|---|---|---|---|
| Benzene | 78 | 171.30 | 1.2 | 1.33 | −1 | 1.10 |
| Pentane, 2,3,4-trimethyl- | 71 | 245.67 | 1.2 | 1.45 | −1 | 0.35 |
| Cyclohexane, 1,4-dimethyl-, trans- | 97 | 280.02 | 1.3 | 1.26 | −1 | 0.059 |
| Hexane, 2,2,4-trimethyl- | 57 | 285.02 | 1.2 | 1.37 | −1 | 0.70 |
| Tricyclo[2.2.1.0(2,6)]heptane, 1,7,7-trimethyl- | 93 | 500.15 | 1.6 | 1.28 | −1 | 0.045 |
| 3-Octene, 4-ethyl- | 69 | 578.11 | 1.5 | 1.27 | −1 | 0.031 |

For sample i, the abundance for peak j, $A_{ij}$ is used to calculate a subscore by $$Q_{ij} = \begin{cases} w_j \text{ if } \begin{cases} S_j = 1 \ \& \ A_{ij} > C_j \\ S_j = -1 \ \& \ A_{ij} < C_j \end{cases}, \\ 0, \text{ otherwise} \end{cases}$$

where the weights $w_j$, the signs $S_j$ and the cutoff values $C_j$ are taken from the sign and cutoff columns in the table. Then, the diagnostic score $Q_i$ for each sample i is $Q_i = \Sigma_j Q_{ij}$. The actual chemical identities of the markers are unlikely to be consistently correct in the table. The physical chemical properties of the marker compounds that cause them to migrate with the specified retention times, and the m/z value of the compounds ionization fragments are the actual content of the algorithm. A comparison of $PaO_2/FIO_2$ ratio and Aggregate breath score over time for each individual animal demonstrates the oxygen exposed animals had an aggregate breath score that became less negative over the course of oxygen exposure.

Figure 1:
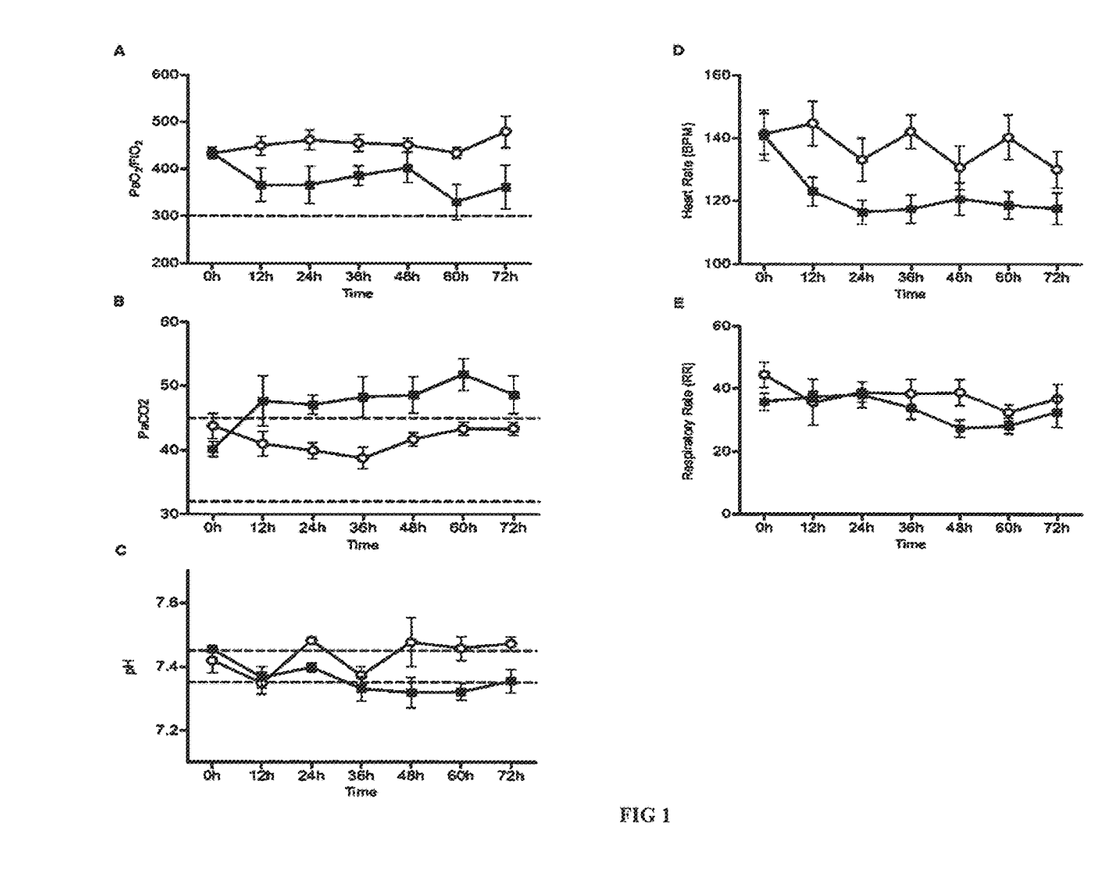
FIG. 1 shows arterial blood gas analysis and vital sign assessment in the oxygen group (closed squares) compared to the air control group (open circles). Line graphs depict PaO2/FiO2 ratio (A), PaCO2 (B), and pH (C) in addition to heart rate (D) and respiratory rate (E). The oxygen group had a decreased PaO2/FiO2 ratio, elevated PaCO2, and decreased pH (p<0.0001 repeated measures ANOVA) when compared to the air control group. Each data point represents mean±SEM. Human reference ranges for upper (red) or lower (blue) range of normal values are indicated by the dashed lines [26].

Results:

Oxygen exposure caused a significant decline in pulmonary function as determined by arterial blood gas analysis and physiological monitoring. Oxygenation as measured by the $PaO_2/FiO_2$ ratio (FIG. 1A) decreased in the oxygen group starting at 12 hours and each subsequent sample collection time point (p=0.0086). Ventilation, measured by $PaCO_2$ (FIG. 1B), remained elevated in the oxygen group as compared to the air control group at all time points after 12 hours (p=0.0099). Blood pH (FIG. 1C) decreased in the air group at the 48, 60, and 72 hour time points (p=0.0157). The mean heart rate (FIG. 1D) was lower in the oxygen group compared to the air group (p>0.05). There was no significant difference in respiratory rate (FIG. 1E) between treatment groups.

Figure 2:
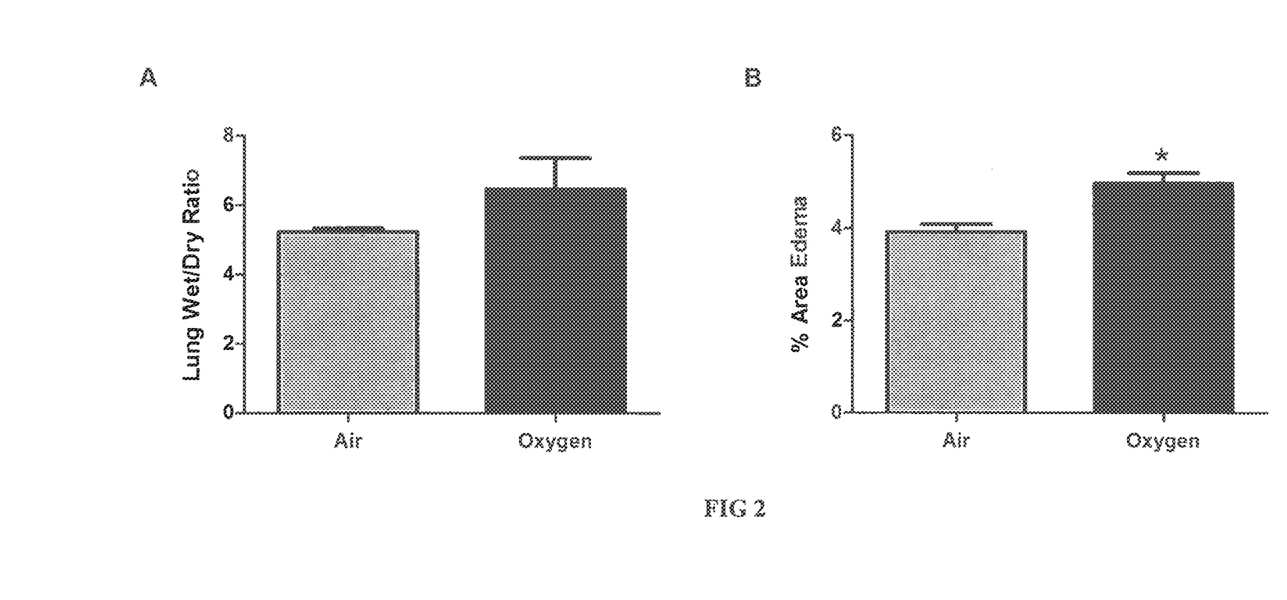
FIG. 2 shows the assessment of pulmonary edema in air control group (gray bar) and oxygen group (black bar). (A) Pulmonary edema, quantified by lung wet-dry ratio, showed an increased trend (p=0.07, student's t-test) in the oxygen group when compared to the air control group. Bars represent mean wet-dry ratio±SEM. (B) On direct histological quantification the percent area of interstitial edema was significantly increased in the oxygen group when compared to the air control group. Bars represent mean percent area edema±SEM. Asterisk represents significance (p=0.0003) as determined by student's t-test.

Oxygen exposure induced pulmonary edema consistent with the exudative phase of $PO_2T$. The wet-dry ratio of the right lung was measured as a gross estimate of pulmonary edema. There was no statistically significant difference in lung weights between groups; however, there was a trend for increased pulmonary edema in the oxygen group (FIG. 2A). Due to the variance in the wet-dry ratios, interstitial edema was directly quantified from histologic sections of the left lung. The percent area of interstitial edema was significantly increased in the oxygen group as compared to the air group (p=0.0003) (FIG. 2B).

Histopathological analysis confirmed that oxygen-exposed swine developed the exudative phase of $PO_2T$. Histologic findings in the oxygen group included interstitial edema, congestion and thickening of alveolar septa by inflammatory cells with and without type II pneumocyte hyperplasis. Alveolar edema was not a predominant finding in any group at 72 hours; however interstitial edema and dilated lymphatics were common findings in oxygen-exposed animals. These pathologic changes are consistent with the exudative phase of $PO_2T$.

Figure 3:
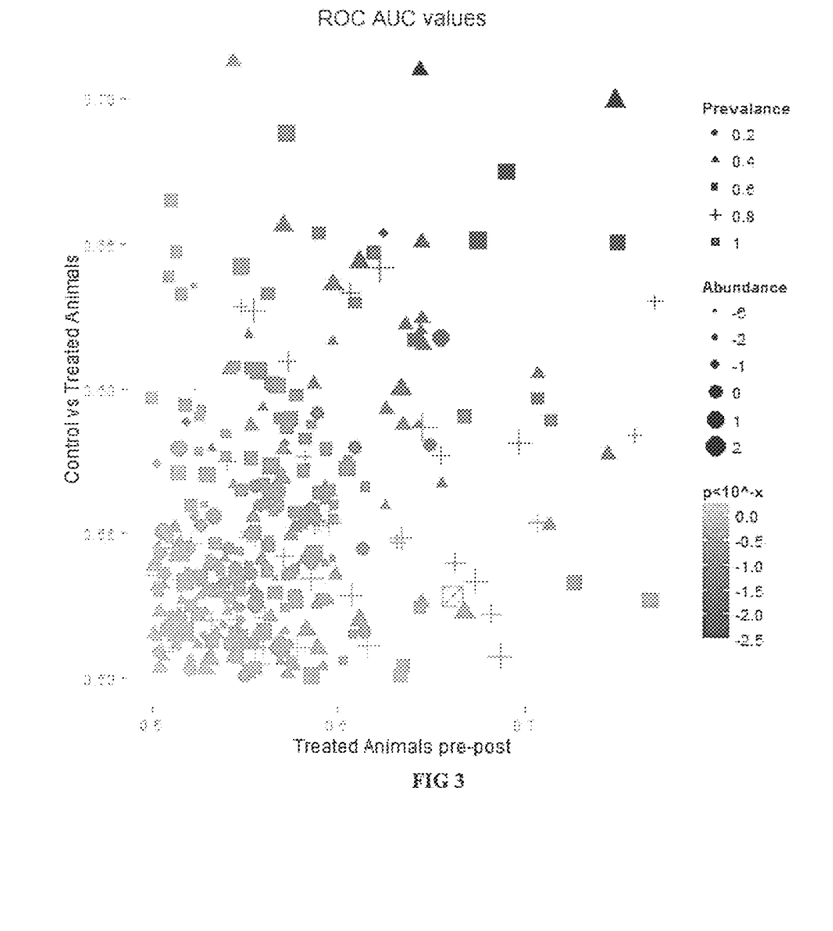

Analysis of VOC content in alveolar breath samples identified candidate biomarkers of oxygen exposure. Each breath exhalate sample produced an average of 700 VOCs with varying abundance. The abundance and prevalence of each VOC peak was aligned across the nine samples from each animal to evaluate changes from baseline. All changes were plotted on an ROC AUC graph with baseline versus exposure samples from oxygen-exposed animals on the x-axis and oxygen-exposed versus room air (control) animals on the y-axis (FIG. 3). VOCs that shifted due to oxygen exposure compared to baseline resulted in a larger x-axis value. VOCs that shifted specific to oxygen exposure compared to room air exposure resulted in a larger y-axis value. Using a preset cut-off value of 0.625 on the x-axis and 0.60 on the y-axis, 18 VOCs were identified as candidate biomarkers for detecting oxygen exposure.

Weighted digital analysis (WDA) led to the development of a predictive breath test for oxygen injury based on 6 VOC compounds. The 18 candidate VOCs were then analyzed by weighted digital analysis to evaluate changes in abundance from baseline to exposure for both oxygen-exposed and room air-exposed subjects. From the WDA analysis, 6 of the 18 candidate VOCs were specific for oxygen exposure and included: benzene; 2,3,4-trimethyl pentane; 1,4-dimethyl-trans cyclohexane; 2,2,4-trimethyl-hexane; 1,7,7-trimethyl-tricyclo heptane; 4-ethyl-3-octene.

Figure 4:
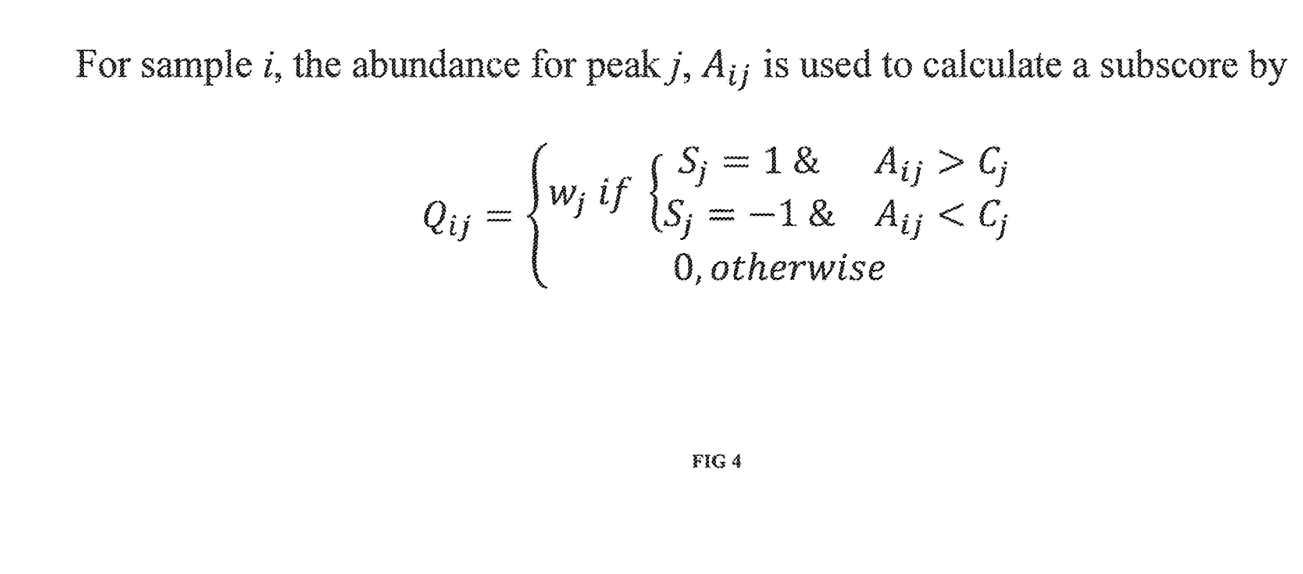
FIG. 4 is Breath score algorithm derived from the six predictive VOCs using the sign, cutoff, and weighting information in table 2. $Q_{ij}$ is the breath score referred to in this work.
Figure 5:
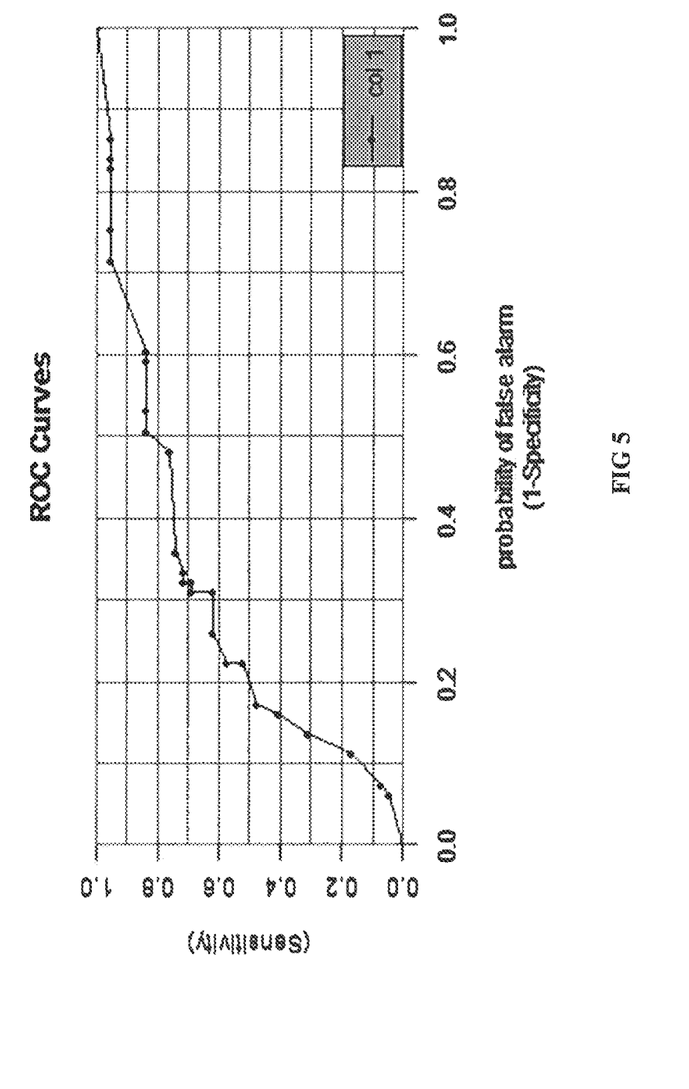
FIG. 5 shows ROC curve for the breath score as a predictor of oxygen exposure. The area under the curve is 0.707 representing a 70.7% probability of predicting oxygen exposure.

Using method similar to Philips et al. [17], an algorithm based on the relative abundance of the six VOCs for $PO_2T$ was developed. The output of this algorithm was a breath score, which reflected the presence of the VOCs in the breath, weighted by the individual C-statistic (AUC of the ROC curve) for oxygen exposure (FIG. 4). The ROC/AUC curve of the breath score had a value of 0.707, indicating a 70.7% probability of predicting oxygen exposure (FIG. 5).

Breath Score Predicts Onset of $PO_2T$ as Determined by Arterial Blood Gas Analysis.

Figure 6:
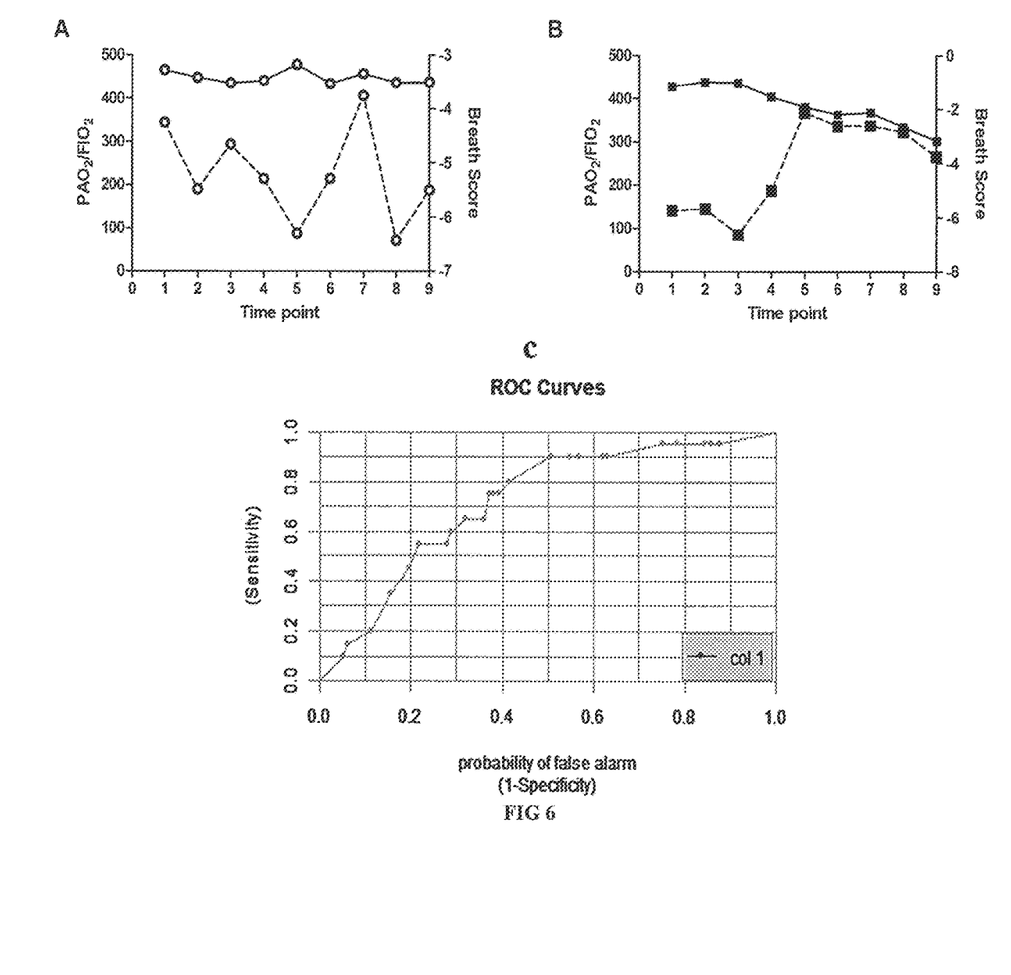
FIG. 6 shows VOC based breath score predicts decrements in $PaO_2/FiO_2$ ratio in oxygen-exposed swine. Line graphs depicting breath score (solid line) and $PaO_2/FiO_2$ ratio (dashed line) in (A) air controls (open circles) and (B) oxygen exposed (closed squares) swine. Breath scores were significantly increased from baseline in oxygen-exposed but not air controls ($p<0.0001$, repeated measures ANOVA). (C) ROC curve for the breath score predicting a $PaO_2/FiO_2$ ratio of <350 mmHg. The area under the curve is 0.72 indicating a 72% probability that the breath score will predict oxygen toxicity as defined by a $PaO_2/FiO_2$ ratio of 350 mmHg or less.

To determine whether the novel algorithm was predictive of $PO_2T$, breath scores for individual swine were then correlated with clinical manifestations of $PO_2T$ defined as a $PaO_2/FiO_2$ ratio of <350 mmHg. Mean breath scores for oxygen-exposed swine (FIG. 6B) were significantly increased (p<0.0001) when compared to air-exposed swine (FIG. 6A). A ROC/AUC curve was generated incorporating the PaO2/FiO2 ratio and the breath score data (FIG. 6C). The predictive value of the breath score to identify animals with PaO2/FiO2 ratio<350 mmHg was 0.72.

DISCUSSION

We identified an exhaled VOC profile that predicted the onset of the exudative phase of PO2T, as defined by histologic and functional endpoints. To our knowledge, this finding represents the first pathologically validated sensitive and specific test for PO2T. PO2T is a limiting factor in the use of oxygen in both military operations and healthcare. Clark et al. [18] demonstrated that normal human lungs can tolerate an FiO2 of 50% or less for an unlimited duration of time without the development of prominent oxygen toxicity. Limited studies in human subjects have demonstrated onset of clinical symptoms between 6 and 12 hours after exposure to a FiO2 of 100% [19], with a change in vital capacity observed after 24 hours of exposure and decrements in static compliance and carbon monoxide diffusing capacity seen by 48 hours of exposure [20]. The maximum safe duration for oxygen exposure between a FiO2 of 50% and 100% is less certain, and the safe upper limit of FiO2 for chronic oxygen therapy in an ambulatory setting is undefined. Because early detection of oxygen toxicity has remained elusive and specific therapy is lacking, limiting FiO2 to the lowest amount necessary to achieve a PaO2>55 mmHg or an oxygen saturation>90% remains the cornerstone of management [5]. Additionally, the military employs a probability-based tool called the unit pulmonary toxic dose to maintain oxygen exposure within safe limits and decrease the risk of PO2T. In both scenarios, the lack of a sensitive and specific test for PO2T has significantly limited the optimal use of supplemental oxygen.

To develop a test specific for PO2T, we analyzed the VOC content of the exhaled breath and developed a breath score based on six VOCs that changed due to oxygen exposure and was predictive of PO2T. We observed that the breath score began to increase after 12 hours of exposure to >95% FiO2, and reached peak levels at the 24 hour time point and remained elevated for the remaining duration of treatment. This pattern was seen in all six VOC compounds and moderately predicted PO2T, when defined as a PaO2/FiO2 ratio less than 350 mmHg. Our predictive value observed for the breath score corroborates previous reports of VOC-based strategies for detecting pulmonary injury [21]. The advantage to using the GC-MS techniques, as illustrated from our study, is the ability to further identify the individual VOCs, which presents opportunities to further investigate the relationship of individual VOCs to the disease of interest.

Of the six VOCs identified, two have been previously identified as components of human breath: benzene [22] and 1, 4-dimethyl-trans cyclohexane [23]. We did not observe any differences in exhaled pentane or ethane between treatment groups, which is similar to the findings reported by van Ooij et al. [13] and to the contrary of several other previous studies, which investigated pentane and ethane as exhaled biomarkers of $PO_2T$ [24, 25]. Unlike previous studies that identified changes in breath methylated alkane contours or specific VOCs with oxygen exposure (18 biomarkers associated with oxygen exposure are identified in this study), a novel set of six VOC biomarkers specific to $PO_2T$ are identified. This process allowed an algorithm to be generate a breath score, which is correlated with clinical endpoints consistent with the development of $PO_2T$ and can be used to predict onset of $PO_2T$ For example, the group of methylated alkanes associated with $PO_2T$ in this study was unique from those identified as predictive of ARDS (octane, acetaldehyde, and 3-methylheptane) [21], indicating that these are not generalized lung injury markers. Interestingly, there was no overlap between the VOCs identified in this study compared with the human diver study conducted by van Ooij et al. [13]. This may be the result of the longer oxygen exposure of this study (72 hours) compared to shorter oxygen exposure duration of van Ooij et al. study [13] (6 hours), in which there was no evidence of pulmonary function decrements in humans.

This is further supported by the observation that the breath score peak did not reach a maximum until the 24-hour time point, or until decrements in the $PaO_2/FiO_2$ ratio were observed. Thus, the difference in oxygen exposure durations may be the largest contributor to the lack of overlap seen in the VOC biomarkers between our study and the van Ooij et al. study [13]. The ability to identify VOC biomarkers of PO2T correlating with decrements in pulmonary function during prolonged hyperoxia exposure has significant potential for applications in clinical and military settings.

Prophetic Example 2: Identification/Validation of VOCs as Diagnostic Markers for Pulmonary Oxygen Toxicity Using Human Breath Samples VOC profiles of breath exhalate samples collected from divers exposed to hyperbaric oxygen during both dry hyperbaric chamber dives and wet pool dives. The samples will be analyzed by two-dimensional gas chromatography. A predictive algorithm specific to PO2T will then be developed from the VOC profiles, and combined with other tests of pulmonary function. The samples will be collected from subjects of two separate ongoing dive studies conducted at the Naval Submarine Research Lab (NSMRL), Groton Conn. and the Navy Experimental Dive Unit (NEDU), Panama City Fla.

The NSMRL study is a double blind randomized sham controlled crossover study with 10 subjects exposed to either 100% oxygen or sham control dives. Dives will be conducted in a hyperbaric chamber to 2.0 ATA (33 fsw) for 6 hrs. Each subject will provide six breath samples collected over the course of the experiment. The samples will be collected at the following time-points: baseline (pre-dive), 2 hrs (during dive), 4 hrs (during dive), 6 hrs (immediately post-dive), 24 hr recovery, and 168 hr recovery. Other endpoints include: pulmonary function tests (PFTs), pulmonary diffusion capacity (DLCO), and exhaled nitric oxide (eNO). The breath samples from this study will be used to identify the human VOC profile associated with PO2T and develop a prototype predictive algorithm.

The NEDU study examines the effects of hyperbaric oxygen exposure on diver physiology. Over the course of this study breath samples will be collected from human subjects exposed to hyperbaric oxygen or hyperbaric air. The study design will be a randomized control trial with 40 subjects performing an in-water dive to 1.35 ATA, randomized to breathe 100% oxygen or air, for 6 hrs. This dive will be repeated daily for 5 days. Breath samples will be collected at initial testing, pre-dives (1 thru 5), post dives (1 thru 5), post 24 hrs, and post 72 hrs. Other endpoints will include PFTs, eNO, and DLCO. The breath samples from this study will be used to validate the predictive algorithm developed from the samples collected at NSMRL.

REFERENCES

1. Clark, J. M. and C. J. Lambertsen, Pulmonary oxygen toxicity: a review. Pharmacol Rev, 1971. 23(2): p. 37-133.
2. Jenkinson, S. G., Oxygen toxicity. New Horiz, 1993. 1(4): p. 504-11.
3. Hedley-Whyte, J., Pulmonary oxygen toxicity: investigation and mentoring. Ulster Med J, 2008. 77(1): p. 39-42.
4. Mikkelsen, M. E., et al., Can we optimize long-term outcomes in acute respiratory distress syndrome by targeting normoxemia? Ann Am Thorac Soc, 2014. 11(4): p. 613-8.
5. Beers, M. F., Oxygen therapy and pulmonary oxygen toxicity, in Fishman's pulmonary diseases and disorders, E. J. Fishman A P, Fishman J A, Grippi M A, Senior R M, Pack A I, Editor. 2008, McGraw-Hill: New York. p. 2613-2630.
6. Jackson, R. M., Pulmonary oxygen toxicity. Chest, 1985. 88(6): p. 900-5.
7. Crapo, J. D., Morphologic changes in pulmonary oxygen toxicity. Annu Rev Physiol, 1986. 48: p. 721-31.
8. Deneke, S. M. and B. L. Fanburg, Normobaric oxygen toxicity of the lung. N Engl J Med, 1980. 303(2): p. 76-86.
9. Freeman, B. A. and J. D. Crapo, Hyperoxia increases oxygen radical production in rat lungs and lung mitochondria. J Biol Chem, 1981. 256(21): p. 10986-92.
10. Dent, A. G., T. G. Sutedja, and P. V. Zimmerman, Exhaled breath analysis for lung cancer. J Thorac Dis, 2013. 5 Suppl 5: p. S540-50.
11. Phillips, M., et al., Point-of-care breath test for biomarkers of active pulmonary tuberculosis. Tuberculosis (Edinb), 2012. 92(4): p. 314-20.
12. Phillips, M., et al., Effect of oxygen on breath markers of oxidative stress. Eur Respir J, 2003. 21(1): p. 48-51.
13. van Ooij, P. J., et al., Nitric oxide and carbon monoxide diffusing capacity after a 1-h oxygen dive to 9 m of sea water. Clin Physiol Funct Imaging, 2014. 34(3): p. 199-208.
14. Council, N. R., Guide for the Care and Use of Laboratory Animals. 1996, Washington, D.C.: The National Academies Press. 140.
15. Phillips, M., et al., Detection of an extended human volatome with comprehensive two-dimensional gas chromatography time-of-flight mass spectrometry. PLoS One, 2013. 8(9): p. e75274.

16. Wang, B., et al., DISCO: distance and spectrum correlation optimization alignment for two-dimensional gas chromatography time-of-flight mass spectrometry-based metabolomics. Anal Chem, 2010. 82(12): p. 5069-81.
17. Phillips, M., et al., Rapid point-of-care breath test for biomarkers of breast cancer and abnormal mammograms. PLoS One, 2014. 9(3): p. e90226.
18. Clark, J. M., Pulmonary limits of oxygen tolerance in man. Exp Lung Res, 1988. 14 Suppl: p. 897-910.
19. Van De Water, J. M., et al., Response of the lung to six to 12 hours of 100 percent oxygen inhalation in normal man. N Engl J Med, 1970. 283(12): p. 621-6.
20. Harabin, A. L., et al., An analysis of decrements in vital capacity as an index of pulmonary oxygen toxicity. J Appl Physiol (1985), 1987. 63(3): p. 1130-5.
21. Bos, L. D., M. J. Schultz, and P. J. Sterk, Exhaled breath profiling for diagnosing acute respiratory distress syndrome. BMC Pulm Med, 2014. 14: p. 72.
22. Poli, D., et al., Exhaled volatile organic compounds in patients with non-small cell lung cancer: cross sectional and nested short-term follow-up study. Respir Res, 2005. 6: p. 71.
23. Sethi, S., R. Nanda, and T. Chakraborty, Clinical application of volatile organic compound analysis for detecting infectious diseases. Clin Microbiol Rev, 2013. 26(3): p. 462-75.
24. Loiseaux-Meunier, M. N., et al., Oxygen toxicity: simultaneous measure of pentane and malondialdehyde in humans exposed to hyperoxia. Biomed Pharmacother, 2001. 55(3): p. 163-9.
25. Morita, S., M. T. Snider, and Y. Inada, Increased N-pentane excretion in humans: a consequence of pulmonary oxygen exposure. Anesthesiology, 1986. 64(6): p. 730-3.
26. Bernard, G. R., et al., The American-European Consensus Conference on ARDS. Definitions, mechanisms, relevant outcomes, and clinical trial coordination. Am J Respir Crit Care Med, 1994. 149(3 Pt 1): p. 818-24.
27. Buszewski et al., Human exhaled air analytics: biomarkers of diseases. Biomed. Chromatogr., 2007, 21, 553-566.
28. Gelfand R, Lambertsen C J (December 1973). "Dynamic respiratory response to abrupt change of inspired CO2 at normal and high PO2". J Appl Physiol 35 (6): 903-13. PMID 4765831. Retrieved 2008-06-13.

What is claimed is:

1. A method of detecting onset of pulmonary oxygen toxicity in a subject comprising:
   a) collecting a breath sample from a subject who has been exposed to an oxygen enriched atmosphere;
   b) detecting in said breath sample the level of a set of volatile organic compounds selected from the group consisting of benzene; 2,3,4-trimethyl pentane; 1,4-dimethyl-trans cyclohexane; 2,2,4-trimethyl-hexane; 1,7,7-trimethyl-tricyclo heptane; and 4-ethyl-3-octene; and
   c) predicting onset of pulmonary oxygen toxicity in said subject.

2. The method according to claim 1, wherein presence of all volatile organic compounds of (b) in said breath sample indicates the onset of pulmonary oxygen toxicity in said subject.

3. The method according to claim 1, further comprising:
   a) collecting a control breath sample from said subject that is collected before exposing said subject to an oxygen enriched atmosphere;
   b) detecting the level of a set of volatile organic compounds selected from the group consisting of benzene; 2,3,4-trimethyl pentane; 1,4-dimethyl-trans cyclohexane; 2,2,4-trimethyl-hexane; 1,7,7-trimethyl-tricyclo heptane; and 4-ethyl-3-octene in said before and after exposure breath samples;
   wherein a significant change in the levels of said volatile organic compounds in the breath samples before and after said exposure to oxygen enriched atmosphere is indicative of onset of pulmonary oxygen toxicity.

4. The method according to claim 3, wherein the changes in the levels of said volatile organic compounds in the samples collected after said exposure to oxygen enriched atmosphere form a pattern, which is significantly different from a pattern of said volatile organic compounds in the control breath sample, and is indicative of onset of $PO_2T$.

5. The method according to claim 1, wherein step c) further comprising
   a) calculating a breath score based on the level of said volatile organic compounds from said breath sample;
   b) predicting a risk of pulmonary injury to said subject if the breath score is greater than −3.5.

6. The method according to claim 5, wherein the breath score between 0.707 and 0.72 is indicative of the onset of pulmonary oxygen toxicity.

7. The method according to claim 1, wherein the level of said volatile organic compound is measured by Gas-Chromatography (GC), GC-lined Mass-Spectrometry (GC-MS), Proton Transfer Reaction Mass-Spectrometry (PTR-MS), Electronic nose device, or Quartz Crystal Microbalance (QCM).

8. The method according to claim 7, wherein the level of said volatile organic compound from said breath sample is measured by Gas-Chromatography-Mass Spectrometry (GC-MS).

9. The method according to claim 1, wherein the subject is a mammal.

10. The method according to claim 9, wherein the subject is a human.

11. A method for preventing or reducing pulmonary oxygen toxicity, comprising the steps of
    a) collecting a breath sample from a subject at risk of developing pulmonary oxygen toxicity;
    b) measuring the level of organic volatile compounds selected from the group consisting of benzene; 2,3,4-trimethyl pentane; 1,4-dimethyl-trans cyclohexane; 2,2,4-trimethyl-hexane; 1,7,7-trimethyl-tricyclo heptane; 4-ethyl-3-octene;
    c) detecting onset of pulmonary oxygen toxicity; and
    d) reducing said subject's exposure to oxygen enriched atmosphere if onset of pulmonary oxygen toxicity is detected in step c).

12. The method of method 11, further comprising treating said subject for pulmonary oxygen toxicity.

13. A method of identifying a set of volatile organic compounds indicative of pulmonary toxicity comprising the steps of:
    a) collecting breath samples from subjects before and after exposing said subjects to an oxygen enriched atmosphere;
    b) determining the levels of volatile organic compounds in said breath samples;
    c) comparing the levels of volatile organic compounds in breath samples taken after said exposure to levels of volatile organic compounds in breath sample taken before said exposure of the same subject;
    d) identifying a set of volatile organic compounds that are significantly different in breath samples collected after said exposure compared to breath samples of the same subjects collected before said exposure;

e) producing a diagnostic algorithm based on profile of said set of volatile organic compounds that is indicative of onset of pulmonary toxicity.

14. The method according to claim 13, wherein a pattern is analyzed with a pattern recognition analyzer.

15. The method according to claim 14, wherein the pattern recognition analyzer comprises at least one algorithm selected from the group consisting of principal component analysis (PCA), artificial neural network algorithms, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

* * * * *